(12) United States Patent
Hudson

(10) Patent No.: US 11,772,390 B2
(45) Date of Patent: Oct. 3, 2023

(54) METHOD AND APPARATUS FOR INKJET PRINTING ABSORBENT ARTICLE COMPONENTS

(71) Applicant: The Procter & Gamble Company, Cincinnati, OH (US)

(72) Inventor: Kasey Marie Hudson, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 260 days.

(21) Appl. No.: 16/995,864

(22) Filed: Aug. 18, 2020

(65) Prior Publication Data

US 2021/0053368 A1 Feb. 25, 2021

Related U.S. Application Data

(60) Provisional application No. 62/889,696, filed on Aug. 21, 2019.

(51) Int. Cl.
*B41J 3/407* (2006.01)
*A61F 13/15* (2006.01)
(Continued)

(52) U.S. Cl.
CPC ......... *B41J 3/407* (2013.01); *A61F 13/15203* (2013.01); *A61F 13/15577* (2013.01);
(Continued)

(58) Field of Classification Search
CPC ....................................................... B41J 3/407
See application file for complete search history.

(56) References Cited

U.S. PATENT DOCUMENTS 9,944,073 B2    4/2018   Strasemeier et al.
10,369,809 B2   8/2019   Oetjen et al.
(Continued)

FOREIGN PATENT DOCUMENTS

CN    101044025 A    9/2007
CN    108602359 A    9/2018

OTHER PUBLICATIONS

PCT Search Report and Written Opinion for PCT/US2020/070424 dated Dec. 3, 2020, 11 pages.

*Primary Examiner* — Scott A Richmond
(74) *Attorney, Agent, or Firm* — Melissa G. Krasovec

(57) ABSTRACT

The present disclosure relates to methods for printing absorbent article substrates. Printing systems herein may include a first printhead and a second printhead, wherein a substrate advances under the first and second printheads. The first printhead ejects ink onto the substrate to define a first printed zone, and the second printhead ejects ink onto the substrate to define a second printed zone. The first printed zone and the second printed zone together define a printed region. The first and second printed zones may be coterminous along respective edges to define a print stitch line extending in the machine direction. The substrate may then be manipulated proximate the print stitch line during a manufacturing process. Positioning the print stitch line proximate a region subject to manipulation may help hide and/or obscure the print stitch line from view. In turn, noticeable visible results of imprecise and/or inconsistent printing operations may be reduced.

13 Claims, 6 Drawing Sheets

(51) Int. Cl.
*B41J 3/54* (2006.01)
*B41J 2/145* (2006.01)
*B41J 2/045* (2006.01)
*A61F 13/513* (2006.01)

(52) U.S. Cl.
CPC .. *A61F 13/15723* (2013.01); *A61F 13/15747* (2013.01); *A61F 13/51394* (2013.01); *B41J 2/04586* (2013.01); *B41J 2/145* (2013.01); *B41J 3/543* (2013.01); *A61F 2013/15243* (2013.01)

(56) References Cited

U.S. PATENT DOCUMENTS

| | | |
|---|---|---|
| 2016/0175166 A1 | 6/2016 | Zink |
| 2018/0257398 A1 | 9/2018 | Strasemeier et al. |
| 2019/0100036 A1* | 4/2019 | Oetjen .................. B41J 3/407 |
| 2020/0085642 A1 | 3/2020 | Schneider et al. |

* cited by examiner

METHOD AND APPARATUS FOR INKJET PRINTING ABSORBENT ARTICLE COMPONENTS

FIELD OF THE INVENTION

The present disclosure relates to apparatuses and methods for inkjet printing absorbent article component substrates advancing in a machine direction, and more particularly, methods and apparatuses with printheads arranged along a cross direction to define print stitch lines in regions of assembled components that are manipulated during assembly.

BACKGROUND OF THE INVENTION

Along an assembly line, various types of disposable absorbent articles, such as diapers and sanitary napkins, may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Webs of material and component parts used to manufacture sanitary napkins may include: backsheets, topsheets, secondary topsheets, absorbent core components, release paper wrappers, and the like. In some configurations, graphics are printed on individual components and/or continuous webs of material used to assemble the absorbent articles. The graphics may be provided by printing ink on substrate materials by various printing methods, such as flexographic printing, rotogravure printing, screen-printing, inkjet printing, and the like.

In some configurations, printing operations are performed separate to the assembly process, such as for example, printing the substrates offline wherein the printed substrates may be stored until needed for production. For example, printing operations may be accomplished on discrete printing lines, separately from converting lines that are dedicated to manufacturing disposable absorbent articles. After printing on the printing lines, the printed substrates are delivered to the converting lines, such as in a form of continuous webs comprising printed images thereon. In addition to or alternatively to offline printing, graphic printing may be done online during the article assembly process. With some article assembly processes, non-contact inkjet printing processes may be utilized due to relatively high degrees of flexibility and ease with regard to the ability to change the design of a printed graphic. In some configurations, a change in graphic design can be implemented by simply inputting commands to a programmed printhead controller to select a desired image to be printed.

However, inkjet printing operations utilized to print substrates incorporated into converting operations is not without challenges in performing such printing processes when attempting to maintain aesthetically pleasing final assemblies. For example, multiple printheads may be needed to create graphics with multiple colors, relatively intricate designs, and/or relatively large sizes. In turn, it may be necessary to arrange multiple printheads along the machine direction and/or cross direction to enable printing at desired widths and/or with desired colors. In some configurations, when a design to be printed on a substrate is wider than the maximum print width of a single printhead, multiple printheads may "stitched" or arranged together along the width of the substrate. As such, printheads may be arranged to print zones that are coterminous to one another along the cross direction to create a contiguous design. In some scenarios, the alignment between printed zones from different printheads may become undesirably offset in the machine direction and/or the cross direction. As such, the offset may result in a visibly noticeable stitch line in the printed region wherein the printed design appears disjointed, and in turn, may detract from aesthetically pleasing aspects of the printed regions. In addition, the aforementioned challenges may be exacerbated in absorbent article assembly processes operating at relatively high speed production rates and/or when printing on substrates that are extensible, such as nonwovens.

Consequently, there remains a need to print substrates and/or components used in absorbent article assembly processes wherein the graphics are printed and/or positioned in such a manner so as to functionally reduce noticeable visible results of imprecise and/or inconsistent printing operations.

SUMMARY OF THE INVENTION

In one form, a method for assembling absorbent articles comprises steps of: providing a substrate extending in a machine direction, the substrate comprising a first surface and an opposing second surface and defining a substrate width in a cross direction; advancing the substrate in the machine direction under a first printhead and a second printhead; ejecting a first ink from the first printhead onto the first surface of the substrate to define a first printed zone comprising: a first side edge separated from a second side edge in the cross direction; ejecting a second ink from the second printhead onto the first surface of the substrate to define a second printed zone comprising: a first side edge separated from a second side edge in the cross direction, wherein the first printed zone and the second printed zone together define a printed region extending in the cross direction from the first side edge of the first printed zone to the second side edge of the second printed zone, and wherein the first printed zone and the second printed zone are coterminous along the second side edge of the first printed zone and the first side edge of the second printed zone to define a print stitch line extending in the machine direction; and manipulating the substrate proximate the print stitch line.

In another form, a method for assembling absorbent articles comprises steps of: providing a substrate extending in a machine direction, the substrate comprising a first surface and an opposing second surface and defining a substrate width in a cross direction; advancing the substrate in the machine direction under the first printhead; ejecting a first ink from a first printhead onto the first surface of the substrate to define a first printed zone comprising: a first side edge separated from a second side edge in the cross direction, and a leading edge separated from a trailing edge in the machine direction, ejecting a second ink from a second printhead onto the first surface of the substrate to define a second printed zone comprising: a first side edge separated from a second side edge in the cross direction, and a leading edge separated from a trailing edge in the machine direction, wherein the leading edge of the first print zone is upstream in the machine direction from the leading edge of the second print zone, wherein the first printed zone and the second printed zone together define a printed region extending in the cross direction from the first side edge of the first printed zone to the second side edge of the second printed zone, and wherein printed region comprises a print stitch line extending along the second side edge of the first printed zone and the first side edge of the second printed zone in the machine direction from the leading edge of the leading edge of the first printed zone to the trailing edge of the second printed zone; and manipulating the substrate proximate the print stitch line.

In yet another form, an absorbent article comprises: a backsheet; a topsheet; an absorbent core positioned between the backsheet and the topsheet; wherein at least one of the backsheet, the topsheet, and the absorbent core comprises a substrate, the substrate comprising a first surface and an opposing second surface; a first ink jetted on the first surface of the substrate that defines a first printed zone comprising: a first side edge separated from a second side edge; a second ink jetted on the first surface of the substrate that defines a second printed zone comprising: a first side edge separated from a second side edge in the cross direction, wherein the first printed zone and the second printed zone together define a printed region extending from the first side edge of the first printed zone to the second side edge of the second printed zone, and wherein the first printed zone and the second printed zone are coterminous along the second side edge of the first printed zone and the first side edge of the second printed zone to define a print stitch line extending in the machine direction; and a fold line extending along the print stitch line.

DETAILED DESCRIPTION OF THE INVENTION

Figure 1:
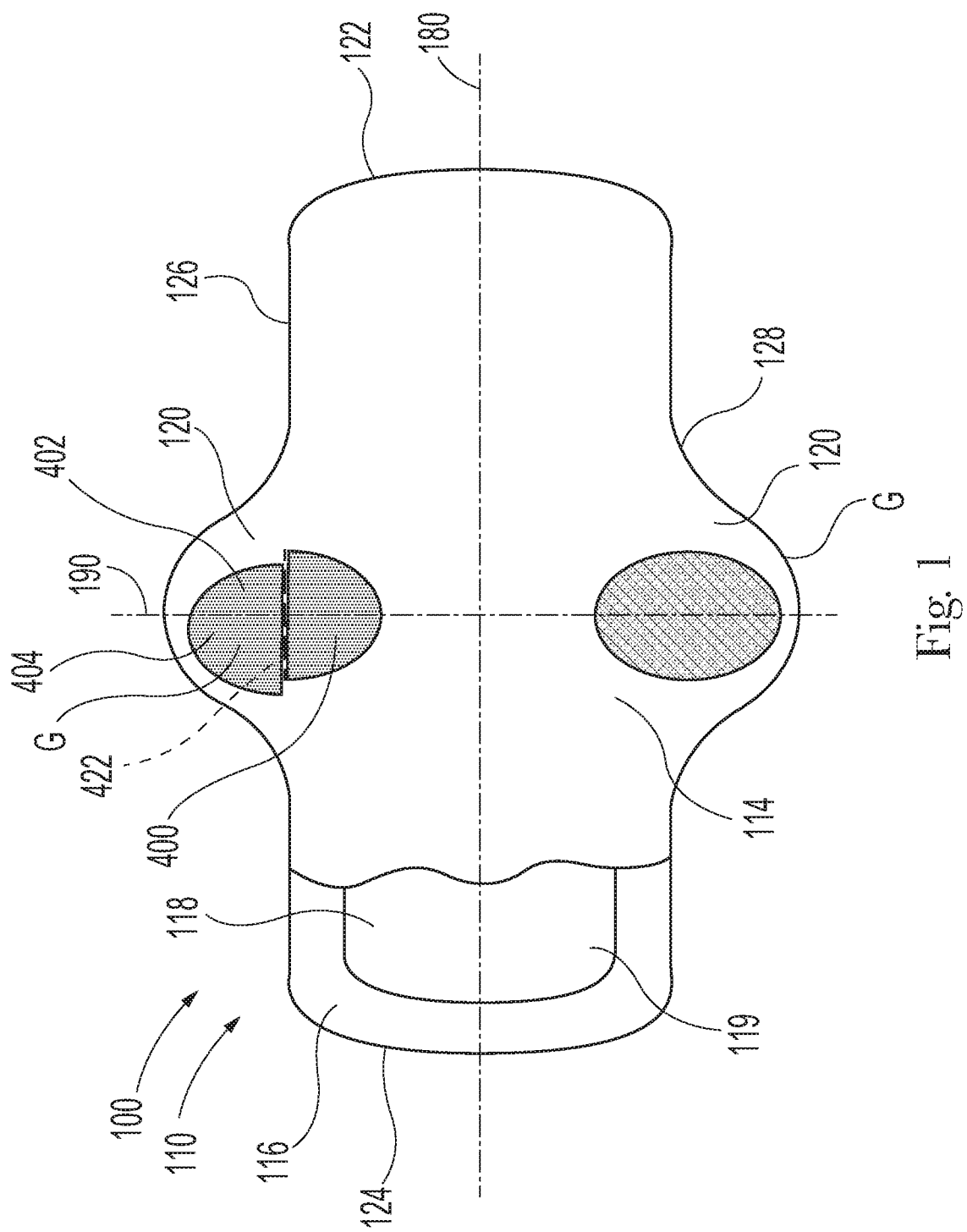
FIG. 1 is a plan view of an absorbent article.

The following term explanations may be useful in understanding the present disclosure: "Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Aspects of the present disclosure relate to methods and apparatuses for printing absorbent article substrates, and in particular, methods and apparatuses having printheads arranged along an advancing substrate. The substrate extends in a machine direction MD, defines a width in a cross direction CD, and includes a first surface and an opposing second surface. As discussed in more detail below, printing systems according to the present disclosure may include a first printhead and a second printhead, wherein the substrate advances in the machine direction under the first printhead and the second printhead. The first printhead ejects a first ink onto the first surface of the substrate to define a first printed zone comprising: a first side edge separated from a second side edge in the cross direction. And the second printhead ejects a second ink onto the first surface of the substrate to define a second printed zone comprising: a first side edge separated from a second side edge in the cross direction. The first printed zone and the second printed zone together define a printed region extending in the cross direction from the first side edge of the first printed zone to the second side edge of the second printed zone. The first printed zone and the second printed zone are coterminous along the second side edge of the first printed zone and the first side edge of the second printed zone to define a print stitch line extending in the machine direction. The substrate may then be manipulated proximate the print stitch line in various ways, such as for example, by folding the substrate;

cutting the substrate; and/or bonding the substrate. As such, positioning the print stitch line proximate to a region that is subject to manipulation may help to hide and/or obscure the print stitch line from view. In turn, noticeable visible results of imprecise and/or inconsistent printing operations may be reduced.

It is to be appreciated that the systems and methods disclosed herein are applicable to work with various types of converting processes and/or machines, such as for example, absorbent article manufacturing, packaging, and/or printing processes. For the purposes of a specific illustration, FIG. 1 shows an example of an absorbent article 100 that may be printed in accordance with the methods and apparatuses disclosed herein. In particular, FIG. 1 shows one example of a plan view of an absorbent article 100 configured as a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 118 and, in some forms, may have a secondary topsheet 119 (STS) instead of acquisition materials. The STS 119 may comprise one or more channels. In some forms, channels in the STS 119 may be aligned with channels in the absorbent core 118. The sanitary napkin 110 may also comprise a lateral axis 190. The sanitary napkin 110 may also comprise wings 120 extending laterally outwardly with respect to a longitudinal axis 180 of the sanitary napkin 110. The wings 120 may be formed by the shape of the of the topsheet 114 and/or backsheet 116. In some configurations, the wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 126 to a midpoint of the second side edge 128. The sanitary napkin 110 may also be provided with additional features commonly found in sanitary napkins as is known in the art.

With regard to the sanitary napkin 110 of FIG. 1, the secondary topsheet 119 incorporating fluid etched stratum of heterogeneous mass may be bonded to, or otherwise attached to the topsheet 114. In some embodiments, thermal point calendaring or other suitable bonding is utilized. In other embodiments, the fluid etched stratum of heterogeneous mass may serve as an absorbent core of an absorbent article. The fluid etched stratum of heterogeneous mass may serve as the topsheet for an absorbent article, the secondary topsheet of an absorbent article. Additionally, an absorbent article may utilize two or more fluid etched stratums of heterogeneous masses within one absorbent article. For example, panty liners and incontinence pads may be formed with the fluid etched stratum of heterogeneous mass positioned between a topsheet and a bottom sheet to function as an absorbent core. Furthermore, the fluid etched absorbent structure having a first layer and a second layer may not include a binder component.

The sanitary napkin 110 may have any shape known in the art for feminine hygiene articles, including the generally symmetric "hourglass" shape, as well as pear shapes, bicycle-seat shapes, trapezoidal shapes, wedge shapes or other shapes that have one end wider than the other.

The topsheet 114, the backsheet 116, and the absorbent core 118 may be assembled in a variety of configurations, including so called "tube" products or side flap products, such as, for example, configurations are described generally in U.S. Pat. Nos. 4,950,264; 4,425,130; 4,321,924; and 4,589,876, all of which are incorporated by reference herein.

As previously mentioned, absorbent articles may be assembled with various components that may be printed off-line, before assembly, or on-line, as part of the assembly process. As such, the absorbent articles herein may include graphics G printed on various components. Thus, in the context of the previous discussion, the apparatuses and methods herein may be used to print substrates configured as continuous substrates and/or discrete components of an absorbent article 100, either off-line or on-line. For example, the apparatuses and methods herein may be utilized in to print graphics on any of the topsheet 114; backsheet 116; secondary topsheet 119; and/or absorbent core 118. For example, the secondary topsheet 114 of the sanitary napkin 110 shown in FIG. 1 includes graphics G that may be printed before, during, and/or after assembly. As discussed in more detail below, the systems and methods herein may be utilized to print such graphics G before, during, and/or after assembly. Although the apparatuses and methods are described herein in the context of the feminine hygiene article 110, such as shown in FIG. 1, it is to be appreciated that the methods and apparatuses herein may be used to print various substrates that can be used with various process configurations and/or absorbent articles, such as for example, taped diapers and diaper pants.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082, all of which are incorporated by reference herein.

Figure 2:
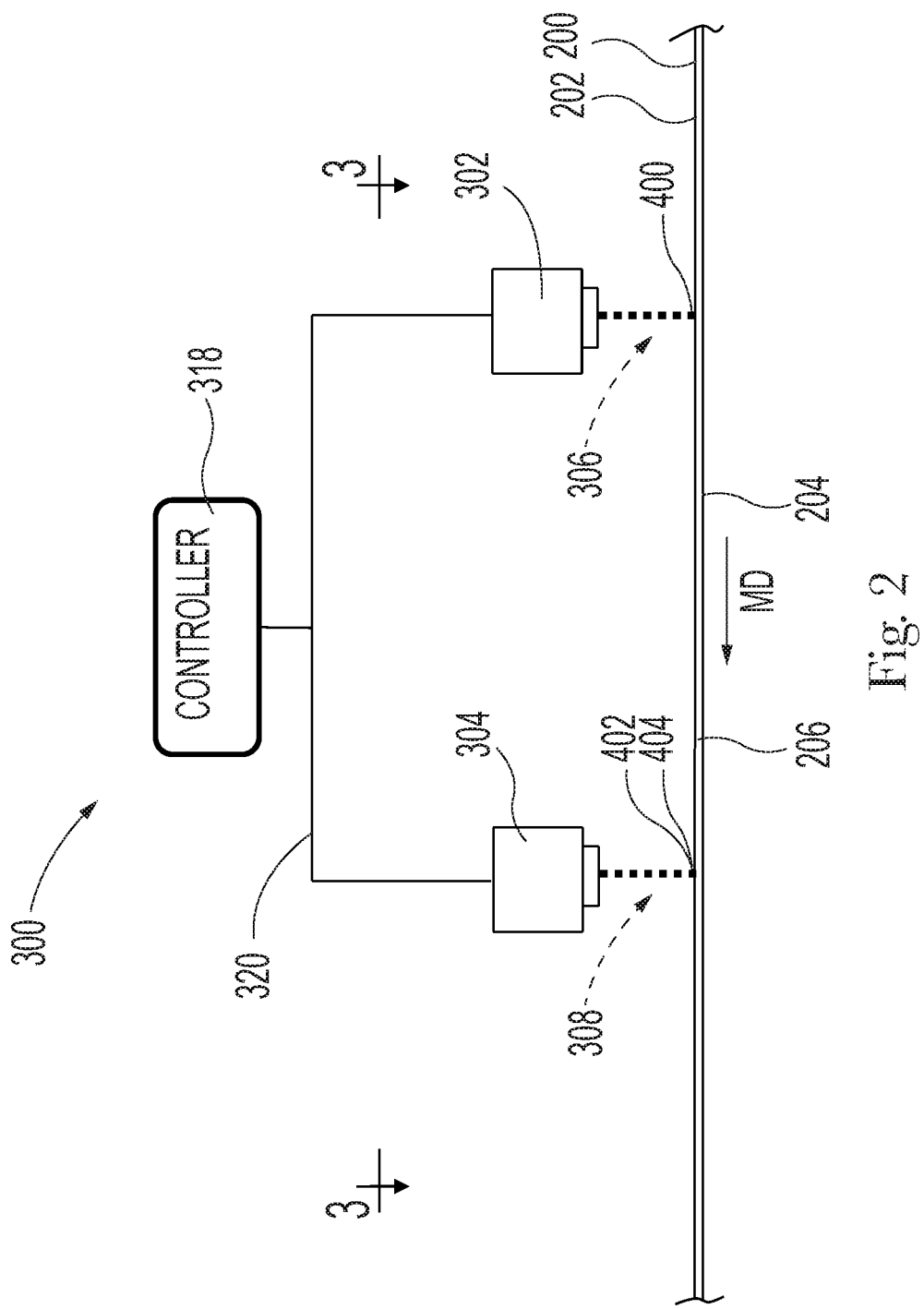
FIG. 2 is a schematic side view of a printing system for printing an advancing substrate.
Figure 3:
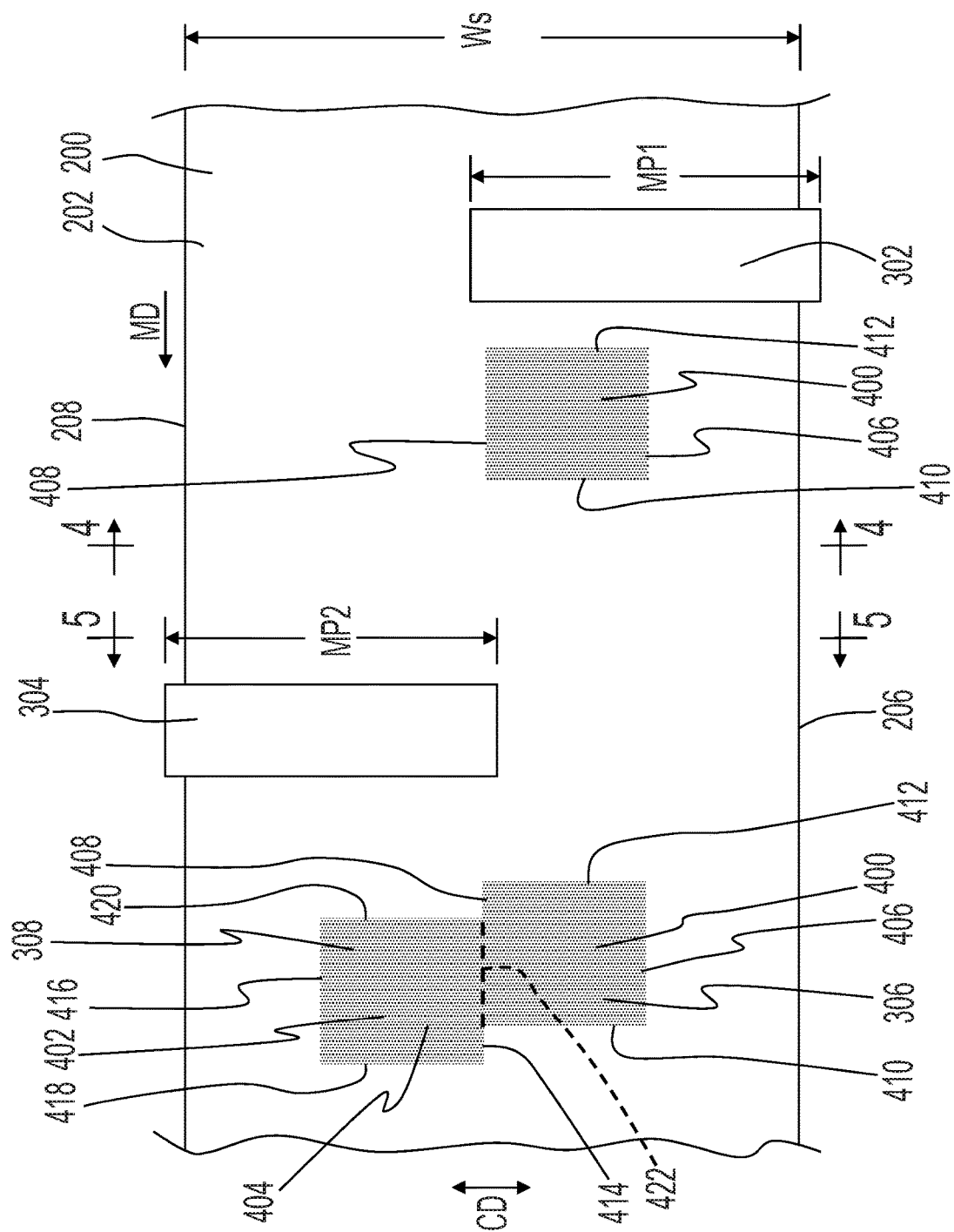
FIG. 3 is a top side view of the advancing substrate and printing system taken along the sectional line 3-3 of FIG. 2.

It is to be appreciated that the printing systems and methods disclosed herein are applicable to work with various types of converting processes and/or machines. For example, FIGS. 2 and 3 show a schematic representation of a converting process including a printing apparatus or system 300 for printing graphics on a substrate 200 advancing in a machine direction MD. The substrate 200 may be a continuous substrate and may include a first surface 202 and an opposing second surface 204. The substrate 200 may also define a width Ws extending in the cross direction CD between a first longitudinal side edge 206 and a second longitudinal side edge 208. It is to be appreciated that the substrate 200 may be subject to additional manufacturing operations, such as combining, bonding, cutting and/or folding operations, during assembly of a product.

Figure 4:
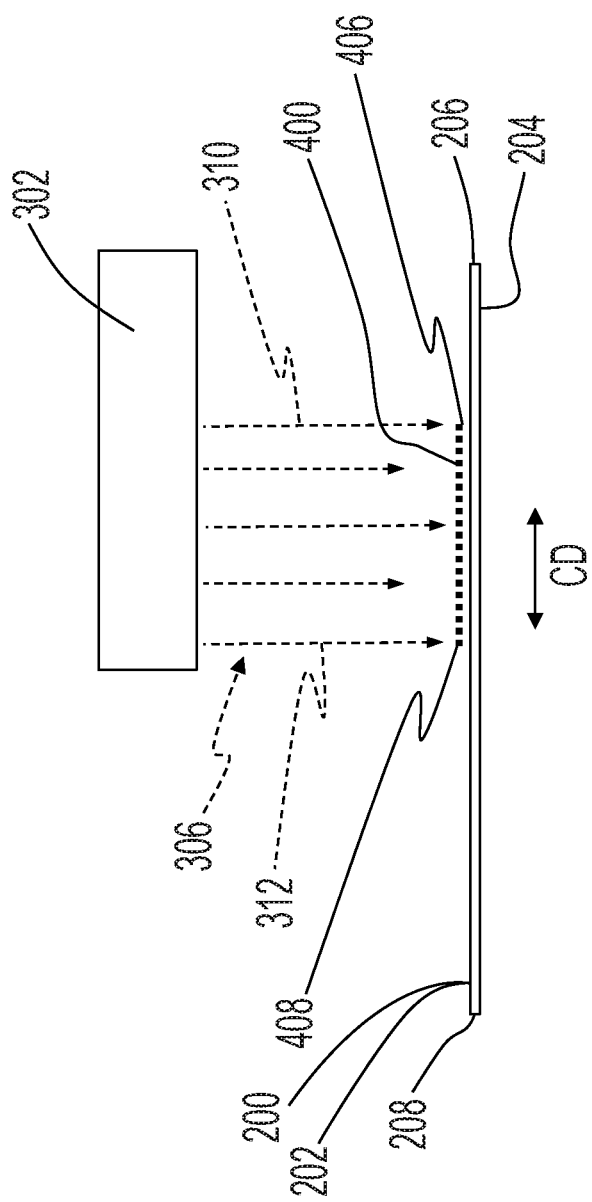
FIG. 4 is a sectional view of the advancing substrate and a first printhead taken along the sectional line 4-4 of FIG. 3.
Figure 5:
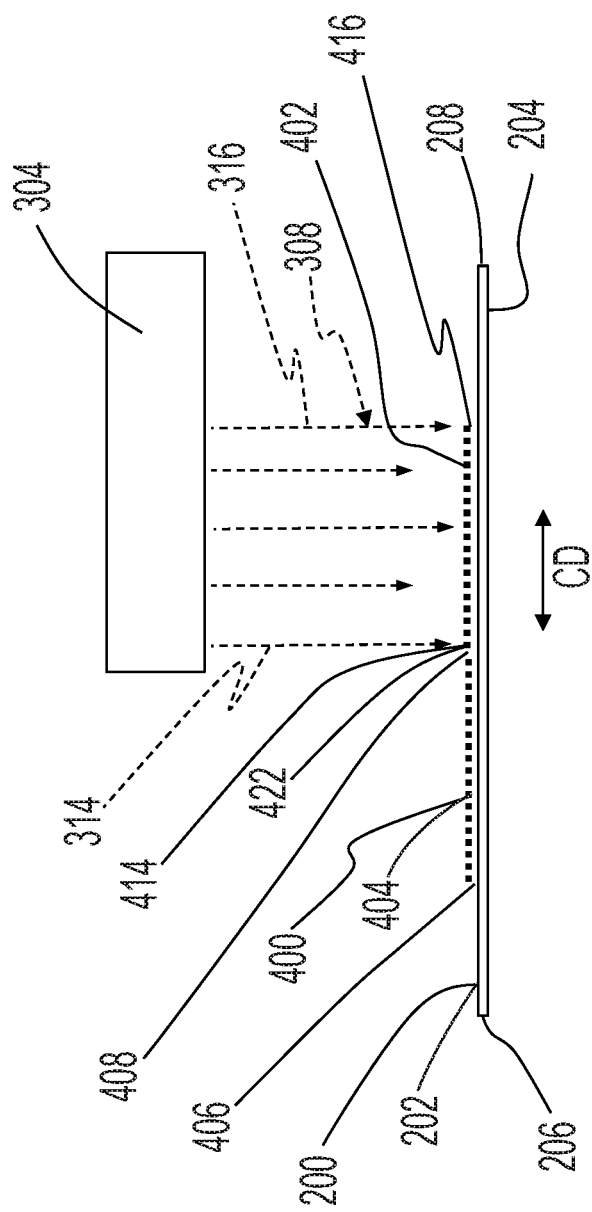
FIG. 5 is a sectional view of the advancing substrate and a second printhead taken along the sectional line 5-5 of FIG. 3.

As shown in FIGS. 2-5, the printing system 300 may include a first printhead 302 and a second printhead 304. During operation, the substrate 200 advances in the machine direction MD under the first printhead 302 and the second printhead 304. The first printhead 302 ejects a first ink 306 onto the first surface 202 of the advancing substrate 200 to define a first printed zone 400 on the first surface 202. The substrate 200 with the first printed zone 400 continues to advance from the first printhead 306 in the machine direction MD under the second printhead 304. As shown in FIGS. 2, 3, and 5, the second printhead 304 ejects a second ink 308 onto the first surface 202 of the advancing substrate 200 to define a second printed zone 402 on the first surface 202. As discussed in more detail below, the first printed zone 400 and the second printed zone 402 together define a printed region 404 on the first surface 202 of the substrate 200. It is to be appreciated that the advancing substrate 200 may be unsupported or supported in areas under the printheads 302, 304. It is to be appreciated that the advancing substrate 200 may be supported in various ways to mitigate movement toward and away from the printheads 302, 304. For example, the second surface 204 of the substrate 200 may be supported by a conveyor having a series of rollers, an advancing belt, and/or a rotating drum.

As shown in FIGS. 3 and 4, the first printed zone includes a first side edge 406 and a second side edge 408 that extend in the machine direction MD. The first side edge 406 is also separated from the second side edge 408 in the cross direction CD. The first printed zone 400 also includes a leading edge 410 separated from a trailing edge 412 in the machine direction MD. In addition, the second printed zone 402 includes a first side edge 414 and a second side edge 416 that extend in the machine direction MD. The first side edge 414 is also separated from the second side edge 416 in the cross direction CD. The second printed zone 402 also includes a leading edge 418 separated from a trailing edge 420 in the machine direction MD.

With continued reference to FIGS. 3 and 5, the first printed zone 400 and the second printed zone 402 together define the printed region 404 that extends in the cross direction CD from the first side edge 406 of the first printed zone 400 to the second side edge 416 of the second printed zone 402. The printed region 404 also extends in the machine direction MD from the trailing edges 412, 420 of the first and second printed zones 400, 402 to the leading edges 410, 418 of the first and second printed zones 400, 402, respectively. With continued reference to FIGS. 3 and 5, the first printed zone 400 and the second printed zone 402 are coterminous along the second side edge 408 of the first printed zone 400 and the first side edge 414 of the second printed zone 402 to define a print stitch line 422 extending in the machine direction MD. The print stitch line 422 is generically represented by a dash line in FIG. 3. It is to be appreciated that the print stitch line 422 may be a straight line or a curved line extending along the machine direction MD.

Although the first printed zone 400 and the second printed zone 402 are generically represented in FIG. 3 as rectangular shapes on the first surface 202 of the substrate 200, it is to be appreciated that the first printed zone 400 and second printed zone 402 may be printed to define various other shapes. It is to be appreciated that the printing system 300 can be configured to print a plurality of printed zones arranged along the machine direction MD and/or cross direction of the substrate 200. It is also to be appreciated that a single printed zone or a single printed region 404 or a plurality of printed zones or regions may form a graphic. As used herein, the term "graphic" refers to images or designs that are constituted by a figure (e.g., a line(s)), a symbol or character, a color difference or transition of at least two colors, or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

Referring now to FIGS. 3-5, the first printhead 302 and the second printhead 304 may be arranged so as to be positioned upstream or downstream with respect to one another along the machine direction MD. In some configurations, the first printhead 302 may be positioned adjacent to the second printhead 304 along the machine direction MD. In some configurations, the first printhead 302 may abut the second printhead 304 in the machine direction MD or there may be a gap in the machine direction MD between the first printhead 302 and the second printhead 304. In some configurations, the second printhead 304 may be positioned various distances from the first printhead 302. For example, in some configurations, the second printhead 304 may be positioned downstream in the machine direction MD from the first printhead 302 by a distance of equal to or less than about 1 meter. The position of the printheads in the machine direction MD may be dependent upon available space in an assembly line, for example.

As shown in FIG. 4, when printing the first printed zone 400, the first printhead 302 may be configured to deposit the first ink 306 on the substrate 200 along the cross direction CD between a first print edge 310 and a second print edge 312. The first print edge 310 of the first printhead 302 may correspond with the first side edge 406 of the first printed zone 400 and/or the second print edge 312 of the first printhead 302 may correspond with the second side edge 408 of the first printed zone 400. As shown in FIG. 5, when printing the second printed zone 402, the second printhead 304 may be configured to deposit the second ink 308 on the substrate 200 along the cross direction CD between a first print edge 314 and a second print edge 316. The first print edge 314 of the second printhead 308 may correspond with the first side edge 414 of the second printed zone 402 and/or the second print edge 316 of the second printhead 304 may correspond with the second side edge 416 of the second printed zone 402. The first printhead 302 and the second printhead 304 may be arranged along the cross direction CD such that the second print edge 312 of first printhead 302 is aligned with first print edge 314 of the second printhead 304. As such, the first printhead 302 and the second printhead 304 may be arranged along the cross direction CD such that first printed zone 400 and the second printed zone 402 are coterminous along the second side edge 408 of the first printed zone 400 and the first side edge 414 of the second printed zone 402.

As shown in FIG. 2, the first printhead 302 is capable of depositing the first ink 304 on the substrate 200 in a first maximum print width MP1 extending in the cross direction CD, and the second printhead 304 is capable of depositing the second ink 308 on the substrate 200 in a second maximum print width MP2 extending in the cross direction CD. The first maximum print width MP1 and the second maximum print width MP2 may be equal or different. The first maximum print width MP1 and/or the second maximum print width MP2 may be equal to, less than, or greater than the substrate width, Ws. In some configurations, the sum of the first maximum print width MP1 and the second maximum print width MP2 may be equal to, less than, or greater than the substrate width, Ws. In some configurations, the first maximum print width MP1 may be equal to or greater than a distance between the first print edge 310 and the second print edge 312 of the first printhead 302, and/or the second maximum print width MP2 may be equal to or greater than a distance between the first print edge 314 and the second print edge 316 of the second printhead 304.

As shown in FIG. 3, the alignment between first printed zone 400 and the second printed zone 402 may be offset in the machine direction MD. For example, the trailing edge 412 of the first printed zone 400 is illustrated as being positioned upstream in the machine direction MD from the trailing edge 420 of the second printed zone 402. The leading edge 410 of the first printed zone 400 may also be positioned upstream in the machine direction MD from the leading edge 418 of the second printed zone 402. In some configurations, the trailing edge 412 of the first printed zone 400 may be positioned downstream in the machine direction MD from the trailing edge 420 of the second printed zone 402, and/or the leading edge 410 of the first printed zone 400 may be positioned downstream in the machine direction MD from the leading edge 418 of the second printed zone 402. It is also to be appreciated that printed features located along and/or between the trailing edges 412, 420 and the leading edges 410, 418 of the first and second printed zones 400, 402, respectively, may also be offset from each other in the machine direction MD and/or the cross direction CD along the print stitch line 422. In turn, the machine direction MD and/or cross direction CD offset between printed features and/or edges of the printed zones 400, 402 may result in a visibly noticeable print stitch line 422, wherein the printed region 404 may appear disjointed.

As previous mentioned, the substrate 200 with the printed region 404 may be incorporated into and/or converted into a component or components of an assembled product in an assembly process. In some configurations, the substrate 200 may be converted into a component of an absorbent article 100. For example, the substrate 200 may be converted into a component that comprises a topsheet 114 with a wing 120, such as discussed above with reference to FIG. 1. During the assembly process, the substrate 200 may be manipulated during various process transformations, such as for example, folding operations, cutting operations, and/or bonding operations. As such, the printing system 300 herein may be configured to print the first printed zone 400 and the second printed zone 402 in positions on the substrate 200 such that the printed substrate 200 is manipulated proximate to and/or along the print stitch line 422 during the assembly process. Such positioning of the print stitch line 422 may function to help to reduce noticeable visible results of imprecise and/or inconsistent printing operations, such as wherein the printed region 404 may appear disjointed along the print stitch line 422.

Figure 6:
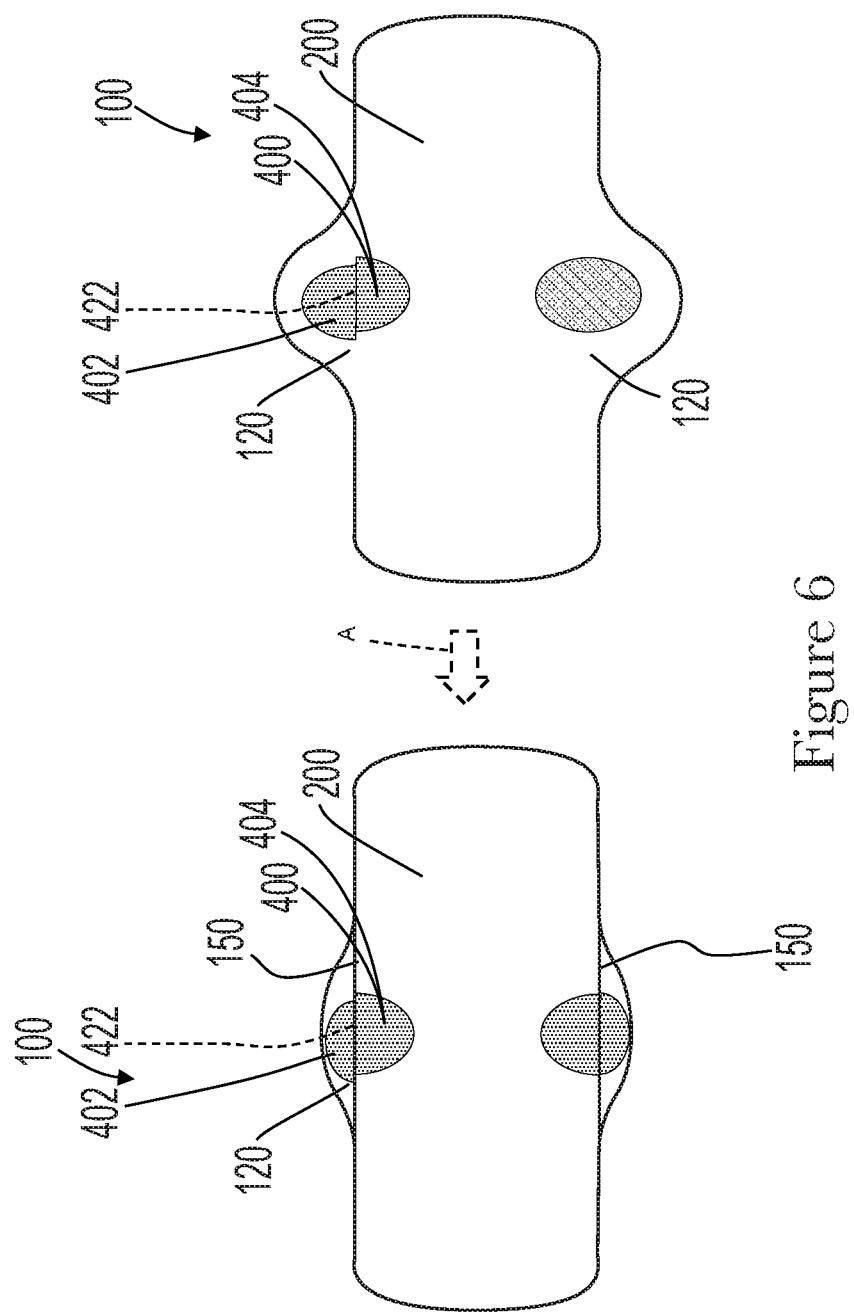
FIG. 6 is a schematic view of an absorbent article assembly process.

For example, FIG. 6 shows an absorbent article such as described above in FIG. 1 advancing through converting operations. As shown in FIG. 6, the absorbent article 100 includes a substrate 200 having been printed with the printing system 300 herein to include a printed region 404 with a print stitch line 422 generically represented with a dashed line. As the absorbent article 100 advances in the machine direction MD, the wings 120 may be folded inward toward each other in the cross direction CD (represented by the dashed arrow "A") so as to define fold lines 150 that extend along the machine direction MD. Examples of such folding operations are disclosed in U.S. Pat. No. 7,500,941 and U.S. Patent Publication No. 2007/0058840A1, both of which are incorporated by reference herein. As shown in FIG. 6, a fold line 150 may also be positioned proximate to and/or along the print stitch line 422. As such, printing the printed region 404 on the substrate 200 such that the print stitch line 422 is positioned proximate to and/or along the fold line 150 may help reduce and/or hide visible appearances of a disjointed printed region 404.

It is to be appreciated that the substrates 200 herein may be advanced in the machine direction MD at various speeds S. For example, the substrate 200 may be configured to advance in the machine direction MD at a speed S of about 0.5 meters/second (m/s) to about 15 m/s, specifically reciting all 1 m/s increments within the above-recited ranges and all ranges formed therein or thereby. In some configurations, the speed S is equal to or greater than about 6 m/s to about 10 m/s.

It is also to be appreciated that the substrate 200 may be configured in various ways. For example, the substrate 200 herein may be configured as a single nonwoven substrate or a single film substrate that defines both the first surface 202 and the second surface 204. It is also to be appreciated that the substrate 200 herein may be configured as a laminate including various layers of substrates bonded together, wherein a nonwoven substrate layer defines the first surface 202 and another substrate layer defines the second surface 204. For example, the substrate 200 may include a nonwoven substrate layer or a film substrate layer that defines the first surface 202 and a second substrate layer defining the second surface 204, wherein the second substrate layer may include a nonwoven or a film.

With reference to FIGS. 2 and 3, it is to be appreciated that the printing apparatus 300 herein may include various quantities of non-contact printheads arranged and/or configured in various ways to deposit inks onto the advancing substrate 200 to create printed regions 404. For example, in some embodiments, the first and second printheads 302, 304 may be configured as inkjet printheads. Inkjet printing is a non-impact dot-matrix printing technology in which droplets of ink are jetted from a small orifice in the printhead directly to a specified position on a substrate to create a graphic. The inkjet printheads herein may be configured to perform different types of inkjet printing, such as for example, "drop-on-demand" and "continuous" inkjet printing.

With "continuous" inkjet printing processes, an ink is supplied under pressure to an inkjet nozzle and forced out through a small orifice. In some configurations, prior to passing out of the nozzle, the pressurized ink stream proceeds through a ceramic crystal, which is subjected to an electric current. The electric current causes a piezoelectric vibration equal to the frequency of an AC electric current. The vibration, in turn, generates the ink droplets from the unbroken ink stream. As such, the ink stream breaks up into a continuous series of drops which are equally spaced and of equal size. Surrounding the jet, at a point where the drops separate from the fluid stream in a charge electrode, a voltage is applied between the charge electrode and the drop stream. When the drops break off from the stream, each drop carries a charge proportional to the applied voltage at the instant at which it breaks off. By varying the charge electrode voltages at the same rate as drops are produced, it is possible to charge every drop to a predetermined level. The drop stream passes between two deflector plates which are maintained at a constant potential that deflects a drop towards one of the plates by an amount proportional to the charge carried. Drops that are uncharged are undeflected and collected into a gutter to be recycled to the ink nozzle. Those drops which are charged, and hence deflected, impinge on a substrate traveling at a high speed at right angles to the direction of drop deflection. By varying the charge on individual drops, a desired pattern can be printed. In some continuous inkjet printing configurations, the printer may utilize pulses of heat to create individual drops of ink, and then may use air to deflect the individual drops of ink.

With "drop-on-demand" inkjet printing processes, an ink is forced under pressure from the printhead through a relatively small orifice in the form of minute droplets by rapid pressure impulses. In some configurations, the orifice may have a diameter of about 0.0024 inches (5-50 microns). The rapid pressure impulses may be generated in the printhead by either expansion of a piezoelectric crystal vibrating at a high frequency or volatilization of a volatile composition (e.g. solvent, water, propellant) within the ink by rapid heating cycles. The piezoelectric crystal expansion causes the ink to pass through the orifice as minute droplets in proportion to the number of crystal vibrations. Thermal inkjet printers employ a heating element within the print head to volatilize a portion of the composition that propels the vast majority of fluid through the orifice nozzle to form droplets in proportion to the number of on-off cycles for the heating element. The ink is forced out of the nozzle when needed to print a spot on a substrate as part of a desired image. The minute droplets may also be energized to achieve an electrical charge and deflected as in the continuous inkjet printing process discussed above. Various inkjet printing processes are more particularly described in U.S. Pat. Nos. 3,465,350; 3,465,351; and 9,211,356.

As previously mentioned, the printing system 300 herein may be configured with various quantities and types of printheads that operate to deposit inks on an advancing substrate at various rates. For example, the first printhead 302 and the second printhead 304 shown in FIG. 3 may be configured as inkjet printheads. As such, when the first printhead 302 fires, a drop of first ink 306 is discharged from an orifice in the first printhead 302. And when the second printhead 304 fires, a drop of second ink 308 is discharged from an orifice in the second printhead 304. The rate at which drops of ink are discharged from an orifice in a printhead is referred to herein as "firing frequency" and may be expressed in units of kilohertz (kHz). In turn, the printheads herein may be configured to operate at various firing frequencies at or below a maximum firing frequency of the printhead. As such, it is to be appreciated that the printing system 300 herein may be configured with various quantities of printheads that may be configured to operate at the same or different firing frequencies. In addition, the printheads herein may be configured with the same or different maximum firing frequencies. For example, in some configurations, the printheads herein may be configured with maximum firing frequencies that are equal to or greater than 5 kHz, and may be configured with maximum firing frequencies of about 5 kHz to about 400 kHz, specifically reciting all 0.1 kHz increments within the above-recited ranges and all ranges formed therein or thereby. In some embodiments, the printheads herein may be configured with maximum firing frequencies of about 20 kHz or about 30 kHz.

It is also to be appreciated that the printing system 300 herein may be configured to operate with various types of inks or ink systems, such as solvent-based, water-based, and ultraviolet (UV) cured inks. An "ink" is a liquid containing coloring matter, for imparting a particular hue to a substrate. An ink may include dyes, pigments, organic pigments, inorganic pigments, and/or combinations thereof. A non-limiting example of an ink would encompass spot colors. Additional non-limiting examples of inks include inks having white color. Additional non-limiting examples of inks include hot melt inks. Additional examples of inks are disclosed in U.S. patent application Ser. No. 16/171,433, filed on Oct. 26, 2018, and U.S. patent application Ser. No. 16/216,083, filed on Dec. 11, 2018, both of which are incorporated herein by reference.

Some primary differences among the ink systems may relate to the method used for drying or curing the ink. For example, solvent-based and water-based inks are dried by evaporation, while UV cured inks are cured by chemical reactions. Inks may also include components, such as solvents, colorants, resins, additives, and (for ultraviolet inks only) UV-curing compounds, that are responsible for various functions. In some embodiments, a multi-stage printing system may be utilized. In some embodiments, to improve ink rub-off resistance, ink compositions used herein may contain a wax. Such waxes may include a polyethylene wax emulsion. Addition of a wax to the ink composition may enhance rub resistance by setting up a barrier which inhibits the physical disruption of the ink film after application of the ink to the fibrous sheet. Based on weight percent solids of the total ink composition, addition ranges for the wax may be from about 0.5% solids to 10% solids. An example polyethylene wax emulsion is JONWAX 26 supplied by S.C. Johnson & Sons, Inc. of Racine, Wis. Some embodiments may utilize inks such as Artistri® Inks available from DuPont™, including 500 Series Acid Dye Ink; 5000 Series Pigment Ink; 700 Series Acid Dye Ink; 700 Series Disperse Dye Ink; 700 Series Reactive Dye Ink; 700 Series Pigment Ink; 2500 Series Acid Dye Ink; 2500 Series Disperse Dye Ink; 2500 Series Reactive Dye Ink; 2500 Series Pigment Dye Ink; 3500 Series Disperse Dye Ink; 3500 Series Pigment Dye Ink; and Solar Brite™ Ink. Ink such as disclosed in U.S. Pat. No. 8,137,721 may also be utilized. Water-based inks that may be utilized are available from Environmental Inks and Coatings Corporation, Morganton, N.C., under the following code numbers: EH034677 (yellow); EH057960 (magenta); EH028676 (cyan); EH092391 (black); EH034676 (orange); and EH064447 (green). Some embodiments may utilize water based inks composed of food-grade ingredients and formulated to be printed directly onto ingestible food or drug products, such as Candymark Series inks available in colors such as black pro, red pro, blue pro, and yellow pro, available from Inkcups located in Danvers, Mass. Other broad ranges of general purpose and specialty inks may also be used, including food grade inks available from Videojet Technologies Inc. located in Wood Dale, Ill. Additional example inks include Collins 186-150-6 LED Cyan Ink; Collins 186-150-7 LED Magenta Ink; Collins 186-150-6 LED Yellow Ink; Collins 186-150-5 LED Black Ink; and Videojet Ink 99-51SR.

It is also to be appreciated that the printing systems 300 herein may be configured to operate with various types of inks that dry when exposed to heat or ambient air for a given time. For example, the inks herein may be configured as solvent or water based inks. In some examples, solvents and/or solvent blends may be used to achieve or help achieve desired physical properties, surface tension, viscosity, or specific gravity or a combination thereof. Example solvents for ink composition may include, without limitation, alcohols, acetates, ketones, glycol ethers, aromatic hydrocarbons, aliphatic naphthas, water, glycols, and combinations thereof. Alcohols may include ethyl alcohol, isopropyl alcohol, N-propyl alcohol, and blends thereof. Acetates may include ethyl acetate, N-propyl acetate, N-butyl acetate, isopropyl acetate, isobutyl acetate, butyl acetate, and blends thereof. Glycol ethers may include ethylene glycol monopropyl ether, ethylene glycol monobutyl ether, diethylene glycol monomethyl ether, diethylene glycol monopropyl ether, propylene glycol monomethyl ether, polyproylene glycol n-propyl ether, and blends thereof. Some solvents may include dipropylene glycol methyl ether, dipropylene glycol n-butyl ether, propolyene glycol, ethylene glycol, dipropylene glycol, and combinations or blends thereof.

In some configurations, the inks herein may be compounded to be printed to meet select physical property ranges. While not wishing to be bound by theory, it is believed certain physical property ranges may affect some characteristics of the printed region 404. For example, the ink may be configured with a surface tension to promote wetting of the substrate 200 by the ink. In another example, the ink may be configured with a viscosity that promotes ink penetration into the substrate 200. In yet another example, the ink 304 may be configured with a specific gravity to promote wetting of the substrate 200 and thereby promoting ink penetration therein.

In some configurations, the ink may have an ink composition that may have a relatively low surface tension compared to the surface tension of fibers that may make up the substrate 200, such as fibers in a nonwoven, or surfaces 202, 204 of the substrate, so as facilitate wetting by the ink composition. As such, the surface tension may provide desirable ink wetting of the substrate. In one nonlimiting example, the ink composition may have a surface tension as measured in dyne/cm at 25 degrees Celsius, which is numerically less than the surface tension of the fibers or surfaces making up the substrate 200, such as a nonwoven. In yet another example, the ink composition may have a surface tension as measured in dyne/cm at 25 degrees Celsius of less than 30.

In some configurations, the ink may have an ink composition that may have a viscosity such that ink penetration occurs upon wetting the substrate 200. It is to be appreciated that various factors may influence ink penetration, such as for example, the ink's resistance to flow, thickness, and/or viscosity. In accordance with one example, the ink composition may have a viscosity in the range of 1 to 30 millipascal seconds. The viscosity measurement is done according to ASTM D 2196-99 Test Method A, where a UL adaptor is utilized and the measurements are made as outlined in ASTM D 2196-99, Test Method A at 25° C. and 60 rpm. Shake time and spindle selection are as indicated within the test method.

In some configurations, the ink may have an ink composition that may have a specific gravity that also promotes wetting of the substrate, such as a nonwoven, and thereby promoting ink penetration therein. An example ink composition may have a specific gravity in the range of 0.830 to 1.050. The specific gravity is measured according to ASTM D 891-95 following Method A and determined at 25° C.

With reference to FIG. 2, it is to be appreciated that the printing apparatus 300 herein may be configured in various ways and may include various types of printing accessories. In some configurations, the printing apparatus 300 may include a corona treater, which may be positioned upstream of the printheads 302, 304. The corona treater may be configured to increase the surface energy of the surface of the substrate 200 to be printed. In some embodiments, the corona treater may be configured to increase the surface energy of the surface to be printed to about 42 dynes/cm. In some configurations, the printing apparatus 300 may print energy curable ink, such as ultraviolet or electron beam curable inks, and thus, may also include an ink curing apparatus. In some configurations, the ink curing apparatus may be in the form of an ultraviolet (UV) light source that may include one or more ultraviolet (UV) lamps, which may be positioned downstream of the printheads 302, 304 to help cure inks deposited onto the substrate 200. In some configurations, the ink curing apparatus may also include an infrared (IR) dryer light source that may include one or more infrared (IR) lamps, which may be positioned downstream of the printheads 302, 304 to help dry water-based or solvent-based inks deposited onto the substrate 200 to form the graphics. In some configurations, the ink curing apparatus may include an electron beam (EB or e-beam) generator that may include one or more e-beam electrodes, which may be positioned downstream of the printhead 302, 304 to help cure inks deposited onto the substrate 200.

Although the above discussion often refers to figures illustrating a printing system having a first printhead 302 and a second printhead 304, it is to be appreciated that the printing systems herein may be configured with more than two printheads arranged in the cross direction CD and/or machine direction MD. In some configurations, the print system 300 herein may include backup printheads, such as disclosed in U.S. Pat. No. 6,811,239. It is also to be appreciated that the first ink 306 and the second ink 308 may be the same colors or may be different colors. For example, the first ink 306 may comprise a first color, and the second ink 308 may comprise a second color different from the first color. In another example, the first ink 306 may comprise a first color, and the second ink may comprise a second color that is the same as the first color. In addition, the printheads herein may be configured to perform single color, multicolor, half tone, and process printing.

"Halftone" or "halftoning" as used herein, sometimes referred to as "screening," is a printing technique that allows for less-than-full saturation of the primary colors. In halftoning, relatively small dots of each primary color are printed in a pattern small enough such that the average human observer perceives as a single color. For example, magenta printed with a 20% halftone will appear to the average observer as the color pink. The reason for this is because, without wishing to be limited by theory, the average observer may perceive the tiny magenta dots and white paper between the dots as lighter, and less saturated, than the color of pure magenta ink. A "base color," as used herein, refers to a color that is used in the halftoning printing process as the foundation for creating additional colors. In some non-limiting embodiments, a base color is provided by a colored ink. Non-limiting examples of base colors may be selected from the group consisting of: cyan, magenta, yellow, black, red, green, and blue-violet. "Black", as used herein, refers to a color and/or base color which absorbs wavelengths in the entire spectral region of from about 380 nm to about 740 nm. "Cyan", as used herein, refers to a color and/or base color which have a local maximum reflectance in the spectral region of from about 390 nm to about 570 nm. In some embodiments, the local maximum reflectance is between the local maximum reflectance of the blue or blue-violet and green local maxima. "Magenta", as used herein, refers to a color and/or base color which have a local maximum reflectance in the spectral region of from about 390 nm to about 490 nm and 621 nm to about 740 nm. "Yellow", as used herein, refers to a color and/or base color which have a local maximum reflectance in the spectral region of from about 571 nm to about 620 nm.

"Process Printing," as used herein, refers to the method of providing color prints using at least three of the primary colors cyan, magenta, yellow and black. Each layer of color is added over a base substrate. In some embodiments, the base substrate is white or off-white in color. With the addition of each layer of color, certain amounts of light are absorbed (those of skill in the printing arts will understand that the inks actually "subtract" from the brightness of the white background), resulting in various colors. CMY (cyan, magenta, yellow) are used in combination to provide additional colors. Non-limiting examples of such colors are red, green, and blue. K (black) is used to provide alternate shades and pigments. One of skill in the art will appreciate that CMY may alternatively be used in combination to provide a black-type color.

It is also to be appreciated that the printed regions 404 may have various print resolutions. For example, the printed region 404 may have a print resolution of at least about 64 dpi, or at least about 100 dpi, or from about 64 dpi to about 1200 dpi, or from about 200 to about 400 dpi, or about 400 dpi or less, reciting for each range every 1 dpi increments therein and all ranges formed therein or thereby in the cross machine direction of the substrate 200, which in some configurations corresponds to the lateral direction of the substrate. In some examples, the printed region 404 may have a print resolution of at least about 10 dpi, or about 6000 dpi or less, or about 1500 dpi or less, or about 100 dpi or less, or from about 10 dpi to about 6000 dpi, reciting for each range every 1 dpi increments therein and all ranges formed therein or thereby in the machine direction of the substrate 200, which in some configurations corresponds to the longitudinal direction of the substrate 200. The ink may also comprise a colorant. In some configurations, the ink 304 comprises cyan, magenta, yellow, black, or combinations thereof.

It is to be appreciated that the printing system 300 herein may also include various additional features. For example, as previously mentioned, the printing system 300 may be configured to print off-line or interact with and/or be configured as a unit operation of a converting line. In some configurations of the printing system 300 may be arranged adjacent the advancing substrate 200, and the printing system 300 may interface and communicate with a controller 318. The controller 318 may be adapted to control the operation of printheads, light sources, metering devices, and/or may allow an operator to manually program the type of graphics to be printed. For example, the printing system 300 may be configured with various features, such as available on the Prosper S20 Ink Jet Printer available from Kodak. In some configurations, the printing system 300 may be configured to interface with other computerized systems and/or networks that may automatically program or command the printing system to print various graphics based on various input, such as sales orders from customers. It is to be appreciated that the controller 318 may be configured in various ways. For example, the controller 318 may be in the form of a personal computer (PC) or a central processing unit (CPU). The controller 318 may also be configured to monitor and affect various operations on a converting line. For example, the controller 318 may send various types of control commands to the converting line based on communications with sensors adjacent the converting line.

It is to be appreciated that the controller 318 may also be configured to communicate with one or more computer systems, such as for example, a programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. In some configurations, process and product data may be stored directly in the aforementioned computer systems or may be located in a separate data historian. In some embodiments, the historian is a simple data table in the controller. In other embodiments, the historian may be a relational or simple database. Common historian applications include Rockwell Automation Factory Talk Historian, General Electric Proficy Historian, OSI PI, or any custom historian that may be configured from Oracle, SQL or any of a number of database applications. It is also to be appreciated that the controller 318 may be configured to communicate with various types of controllers and inspection sensors configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; and 8,244,393; and European Patent No. EP 1528907 B1, all of which are incorporated by reference herein.

As shown in FIG. 2, the printheads 302, 304 may be in communication with the controller 318 through a communication network 320. As such, it is to be appreciated that the controller 318 may be physically located near the advancing substrate 200 and/or the printing system 300 and/or may be located at another location and in communication with the printing system 300 via a wired and/or wireless network 320. In some embodiments, the communication network 320 is configured as a non-deterministic communication network, such as for example, Ethernet or Ethernet IP (industrial protocol) communication network.

It is also to be appreciated that the printing systems 300 herein may be configured to print printed regions 404 at desired print resolutions on a substrate 200, wherein the printed regions may form graphics G, such as shown in FIG.

1 and discussed above with reference to absorbent articles assembled with various components that may be printed off-line, before assembly, or on-line, as part of the assembly process. Thus, in the context of the previous discussion, the printing system 300 herein may be used to print substrates and components of an absorbent article 100, either off-line or on-line. For example, the printing system 300 herein may be utilized to print printed regions 404 on a sanitary napkin to form graphics on any of the topsheet 114; secondary topsheet 119, backsheet 116; wings 120; and/or absorbent core 118 before or during the manufacture of an absorbent article 100. In other examples, the printing system 300 herein may be utilized to print printed regions on a diaper to form graphics on any of a topsheet; backsheet; absorbent core; leg cuffs; waist features; side panels; connection zones; fastening elements; and/or belts.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling absorbent articles, the method comprising steps of:
   providing a substrate extending in a machine direction, the substrate comprising a first surface and an opposing second surface and defining a substrate width in a cross direction;
   advancing the substrate in the machine direction under a first printhead and a second printhead;
   ejecting a first ink from the first printhead onto the first surface of the substrate to define a first printed zone comprising: a first side edge separated from a second side edge in the cross direction;
   ejecting a second ink from the second printhead onto the first surface of the substrate to define a second printed zone comprising: a first side edge separated from a second side edge in the cross direction, wherein the first printed zone and the second printed zone together define a printed region extending in the cross direction from the first side edge of the first printed zone to the second side edge of the second printed zone, and wherein the first printed zone and the second printed zone are coterminous along the second side edge of the first printed zone and the first side edge of the second printed zone to define a print stitch line extending in the machine direction; and
   manipulating the substrate proximate the print stitch line; and
   converting the substrate into a component of an absorbent article,
   wherein the component comprises a topsheet and a wing, and
   wherein the step of manipulating further comprises folding the topsheet and the wing along the print stitch line.

2. The method of claim 1, wherein the step of manipulating further comprises at least one of: folding the substrate; cutting the substrate; and bonding the substrate.

3. The method of claim 1, wherein the print stitch line is a straight line.

4. The method of claim 1, wherein the print stitch line is a curved line.

5. The method of claim 1, wherein the first printhead is capable of depositing ink on the substrate in a first maximum print width extending in the cross direction from a first print edge to a second print edge, and wherein second printhead is capable of depositing ink on the substrate in a second maximum print width extending in the cross direction from a first print edge to a second print edge.

6. The method of claim 5, wherein at least one of the first maximum print width and the second maximum print width is less than the substrate width.

7. The method of claim 5, wherein the sum of the first maximum print width and the second maximum print width is greater than or equal to the substrate width.

8. The method of claim 5, further comprising a step of arranging the first printhead and the second printhead such that the second print edge of first printhead is aligned with the first print edge of the second printhead.

9. The method of claim 5, wherein the first print edge of the first printhead corresponds with the first side edge of the first printed zone.

10. The method of claim 9, wherein the second print edge of the first printhead corresponds with the second side edge of the first printed zone.

11. A method for assembling absorbent articles, the method comprising steps of:
   providing a substrate extending in a machine direction, the substrate comprising a first surface and an opposing second surface and defining a substrate width in a cross direction;
   advancing the substrate in the machine direction under the first printhead;
   ejecting a first ink from a first printhead onto the first surface of the substrate to define a first printed zone comprising: a first side edge separated from a second side edge in the cross direction, and a leading edge separated from a trailing edge in the machine direction,
   ejecting a second ink from a second printhead onto the first surface of the substrate to define a second printed zone comprising: a first side edge separated from a second side edge in the cross direction, and a leading edge separated from a trailing edge in the machine direction,
   wherein the leading edge of the first print zone is upstream in the machine direction from the leading edge of the second print zone, wherein the first printed zone and the second printed zone together define a printed region extending in the cross direction from the first side edge of the first printed zone to the second side edge of the second printed zone, and wherein printed region comprises a print stitch line extending along the second side edge of the first printed zone and the first side edge of the second printed zone in the machine direction from the leading edge of the leading edge of the first printed zone to the trailing edge of the second printed zone; and manipulating the substrate proximate the print stitch line converting the substrate into a component of an absorbent article, wherein the component comprises a topsheet and a wing, and wherein the step of manipulating further comprises folding the topsheet and the wing along the print stitch line.

12. The method of claim 11, wherein the step of manipulating further comprises at least one of: folding the substrate; cutting the substrate; and bonding the substrate.

13. The method of claim 11, wherein the print stitch line is a straight line.

* * * * *